United States Patent [19]

Hagemann et al.

[11] Patent Number: 4,980,510
[45] Date of Patent: Dec. 25, 1990

[54] PROCESS FOR PREPARING THIOPHENOLS AND NOVEL THIOPHENOLS

[75] Inventors: Hermann Hagemann, Leverkusen; Klaus Sasse, Bergisch-Gladbach; Reiner Fischer, Monheim, all of Fed. Rep. of Germany

[73] Assignee: Bayer Aktiengesellschaft, Leverkusen, Fed. Rep. of Germany

[21] Appl. No.: 219,103

[22] Filed: Jul. 14, 1988

[30] Foreign Application Priority Data

Aug. 3, 1987 [DE] Fed. Rep. of Germany ....... 3725640

[51] Int. Cl.$^5$ .................. C07C 315/04; C07C 319/02
[52] U.S. Cl. ....................... 568/29; 568/36; 568/63
[58] Field of Search .............. 568/29, 36, 63

[56] References Cited

U.S. PATENT DOCUMENTS 3,374,274   3/1968   Spainhour ........................... 568/68
3,949,002   4/1976   Feasey et al. ....................... 568/29

OTHER PUBLICATIONS

J. Org. Chem. 28, 3077–3082 (1963), D. Walker et al.
Houben Weyl, E11/I (1985), pp. 32–62 and 158–161.

*Primary Examiner*—Mary E. Ceperley
*Attorney, Agent, or Firm*—Sprung Horn Kramer & Woods

[57] ABSTRACT

Thiophenols of the formula t,10
in which
$R^1$, $R^2$, $R^3$ and $R^4$ independently of each other each stand for hydrogen, halogen, nitro, alkyl, alkoxy, alkylthio, alkoxyalkyl, alkylthioalkyl, haloalkyl, haloalkoxy or alkylcarboxyl, optionally substituted aryl or optionally substituted hetaryl, $R^5$ stands for alkyl, alkoxyalkyl, alkylthioalkyl, haloalkyl, alkenyl, haloalkenyl, optionally substituted aryl or optionally substituted hetaryl, and X stands for carbonyl, sulphinyl or sulphonyl can be obtained by reacting halobenzenes of the formula

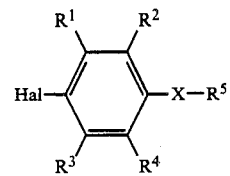

in which
Hal stands for halogen, first with sodium hydrogen sulphide or sodium sulphide in the presence of a diluent to form compounds of the formula

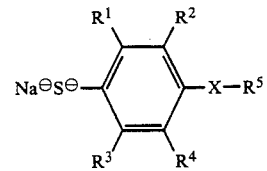

and then adding an acid to form the thiophenol, some of the thiophenols are novel and all can be used to form aryethioaminopyridides which are employed as herbicides.

4 Claims, No Drawings

PROCESS FOR PREPARING THIOPHENOLS AND NOVEL THIOPHENOLS

The present invention relates to a novel process for preparing novel and known thiophenols and to novel thiophenols.

Thiophenols can be used as intermediates for the synthesis of herbicidal active substances. Furthermore, these compounds can be employed for preparing dyestuffs, pharmaceuticals and rubber auxiliaries. The novel and known thiophenols are particularly suitable for preparing novel arylthioaminopyrimidines which are employed as herbicides.

It is already known that the thiophenols of the type of the compounds of the general formula (I) described below are obtained by reacting halobenzenes with alkali metal disulphides at a ratio of 1:1 to 2:1, preferably 2:1, followed by acidification and digestion of the pretipitate obtained with sodium sulphite solution at temperatures between 90° and 100° C. After the insoluble component is separated off by filtration, the filtrate is acidified to give the desired thiophenol in a yield of less than 30%. The portion of the reaction mixture which cannot be extracted with sodium sulphite solution is then dissolved in aqueous sodium sulphide solution, some of it is reprecipitated with acid and again digested with sodium sulphite solution (cf. DE-OS German Published Specification) No. 2,156,345).

The disadvantage of this process is that the reaction steps, that is the addition of sodium sulphide solution etc., must be repeated several times to obtain better yields. Conducting a reaction with such expenditures of time and material is extremely unsuitable for industrial exploitation.

Furthermore, it is known that thiophenols of the above type can be obtained by first converting thiophenols to thioacetic acid derivatives, acetylating according to Friedel-Crafts, for example, or benzoylating in a conventional manner and freeing the acylated thiophenols by oxidative cleavage. To obtain pure products, the disulphanes which are also formed must be reduced (J. Org. Chem. 28, 3077-3082 (1963)).

Moreover, a few further methods for preparing thiophenols of the above type are also suitable, such as are described in the handbook Houben-Weyl "Methoden der Organischen Chemie" Vol. E11 Part 1, p. 32-62 (1985) for thiophenols, for example those methods which proceed through diazotization of the corresponding amino compound. The disadvantage of all these methods is that, as already discussed above, they are multi-step procedures and considerably more expensive and/or that in particular the readily accessible halobenzenes of the formula (II) cannot be used as starting materials.

It has been found that thiophenols of the formula (I)

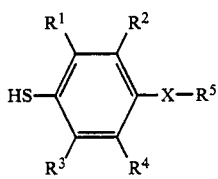

in which $R^1$, $R^2$, $R^3$ and $R^4$ independently of each other each stand for hydrogen, halogen, nitro, alkyl, alkoxy, alkylthio, alkoxyalkyl, alkylthioalkyl, haloalkyl, haloalkoxy or alkylcarboxyl, optionally substituted aryl or optionally substituted hetaryl, $R^5$ stands for alkyl, alkoxyalkyl, alkylthioalkyl, haloalkyl, alkenyl, haloalkenyl, optionally substituted aryl or optionally substituted hetaryl, and X stands for carbonyl, sulphinyl or sulphonyl by reacting halobenzenes of the formula (II)

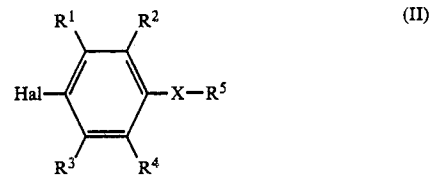

in which $R^1$, $R^2$, $R^3$, $R^4$, $R^5$ and X have the abovementioned meaning and Hal stands for halogen, first with sodium hydrogen sulphide or sodium sulphide in the presence of a diluent to form compounds of the formula (III)

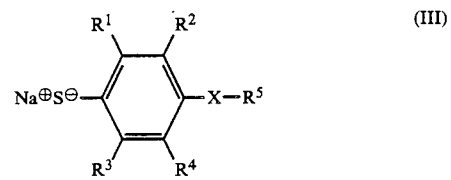

in which $R^1$, $R^2$, $R^3$, $R^4$, $R^5$ and X have the abovementioned meaning, and then adding an acid.

It must be considered particularly surprising that by using the process according to the invention the desired thiophenols can be obtained in high yields and purities, since, based on prior art, it was to be expected that their strongly nucleophilic thiophenolate anions would react in the alkaline reaction mixture with still unconverted halobenzene of the formula (II) with the formation of sulphanes (cf. "Methoden der organischen Chemie" Houben-Weyl, Vol. E11, part 1, p. 158 ff).

The process according to the invention is characterized by a number of advantages. These include for example conducting the reaction in one step and the simple work-up. A further advantage of the process according to the invention is that the halobenzenes of the formula (II) which are required as starting compounds are readily accessible.

The carbon chains in the individual radicals are each straight-chain or branched. The radicals may each be monosubstituted or polysubstituted by identical or different substituents.

By using the process according to the invention, those thiophenols of the formula (I) in which $R^1$, $R^2$, $R^3$ and $R^4$ independently of each other each stand for hydrogen, fluorine, chlorine, bromine, iodine, nitro, $C_1$-$C_6$-alkyl, $C_1$-$C_6$-alkoxy, $C_1$-$C_6$-alkylthio, $C_1$-$C_4$-alkoxy-$C_1$-$C_6$-alkyl, $C_1$-$C_4$-alkylthio-$C_1$-$C_6$-alkyl, halo-$C_1$-$C_6$-alkyl, halo-$C_1$-$C_6$-alkoxy or $C_1$-$C_6$-alkylcarboxyl, optionally substituted aryl having 6 to 10 carbon atoms or optionally substituted hetaryl having 5 to 7 ring atoms, examples of aryl and hetaryl substituents being halogen, nitro, $C_1$-$C_4$-alkyl, $C_1$-$C_4$-alkoxy, $C_1$-$C_4$-alkylthio and halo $C_1$-$C_4$-alkyl and hetaryl having 1 or 2 identical or different heteroatoms such as nitrogen, sulphur or oxygen and in particular standing for pyridyl or pyrimidyl substituted by the abovementioned substituents, and aryl standing in particular for phenyl or naphthyl substituted by the abovementioned substituents, $R^5$ stands for $C_1$-$C_{12}$-alkyl, $C_1$-$C_6$-alkoxy-$C_1$-$C_{12}$-alkyl, $C_1$-$C_6$-alkylthio-$C_1$-$C_{12}$-alkyl, halo-$C_1$-$C_{12}$-alkyl, $C_2$-$C_{10}$-alkenyl, halo-$C_2$-$C_{10}$-alkenyl, optionally substituted aryl having 6 to 10 carbon atoms or optionally substituted hetaryl having 5 or 6 ring atoms, examples of aryl and hetaryl substituents being halogen, nitro, $C_1$-$C_4$alkyl, $C_1$-$C_4$-alkoxy, $C_1$-$C_4$-alkylthio and halo-$C_1$-$C_4$-alkyl and hetaryl having 1 or 2 identical or different heteroatoms such as nitrogen, sulphur, or oxygen and standing in particular for pyridyl or pyrimidyl substituted by the abovementioned substituents, aryl standing in particular for phenyl or naphthyl substituted by the abovementioned substituents, and X stands for carbonyl, sulphinyl or sulphonyl. Particularly preferred are those compounds of the formula (I) in which $R^1$, $R^2$, $R^3$ and $R^4$ independently of each other each stand for hydrogen, fluorine, chlorine, bromine, nitro, $C_1$-$C_4$-alkyl, $C_1$-$C_4$-alkoxy, $C_1$-$C_4$-alkylthio, $C_1$-$C_2$-alkoxy-$C_1$-$C_4$-alkyl, $C_1$-$C_2$-alkylthio-$C_1$-$C_4$-alkyl, halo-$C_1$-$C_4$-alkyl, halo-$C_1$-$C_4$-alkoxy or $C_1$-$C_4$-alkylcarboxyl, and for, in each case, optionally substituted phenyl, naphthyl, pyridyl or pyrimidyl, examples of substituents being fluorine, chlorine, bromine, nitro, methyl, ethyl, methoxy, ethoxy, methylthio, ethylthio and halo-$C_1$-$C_2$-alkyl.

$R^5$ stands for $C_1$-$C_{10}$-alkyl, $C_1$-$C_4$-alkoxy-$C_1$-$C_{10}$-alkyl, $C_1$-$C_4$-alkylthio-$C_1$-$C_{10}$-alkyl, halo-$C_1$-$C_{10}$-alkyl, $C_2$-$C_5$-alkenyl, halo-$C_2$-$C_5$-alkenyl, and for, in each case, optionally substituted phenyl, pyridyl, or pyrimidyl, examples of substituents being fluorine, chlorine, bromine, nitro, methyl, ethyl, methoxy, ethoxy, methylthio, ethylthio and halo-$C_1$-$C_2$-alkyl (particularly trifluoromethyl), and X stands for carbonyl, sulphinyl or sulphonyl.

In particular, the compounds of the formula (I) in which $R^1$ and $R^4$ independently of each other each stand for hydrogen, fluorine, chlorine or methyl, $R^2$ and $R^3$ stand for hydrogen, and $R^5$ stands for $C_1$-$C_9$-alkyl, $C_1$-$C_2$-alkoxy-$C_1$-$C_9$alkyl, $C_1$-$C_2$-alkylthio-$C_1$-$C_9$-alkyl, halo-$C_1$-$C_9$-alkyl, halogen standing for fluorine and/or chlorine, $C_2$-$C_4$-alkenyl, halo-$C_2$-$C_4$-alkenyl, halogen standing for fluorine and/or chlorine, and for optionally substituted phenyl, examples of substituents being fluorine, chlorine, nitro, methyl, ethyl, methoxy, ethoxy and trifluromethyl, and X stands for carbonyl, sulphinyl or sulphonyl, are obtained.

If, for example, 4-(3,3-dimethylbutyro)-chlorobenzene and sodium hydrogen sulphide are used as starting materials, the reaction sequence of the process according to the invention can be represented by the following equations:

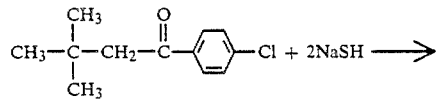

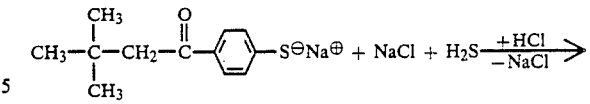

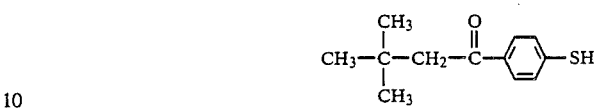

The halobenzenes which are required as starting materials for carrying out the process according to the invention are in general defined by the formula (II). Preferred compounds of the formula (II) are those in which $R^1$, $R^2$, $R^3$, $R^4$, $R^5$ and X stand for those radicals which have already been mentioned in connection with the description of the substances of the formula (I) as preferred or particularly preferred for these substituents. Hal stands preferably for fluorine or chlorine.

The halobenzenes of the formula (II) are known or can be prepared by known procedures, for example by Friedel-Craft acylation.

The process according to the invention is carried out in the presence of a suitable diluent.

Suitable diluents are virtually all inert organic solvents The include in particular N-methylpyrrolidone, dimethylformamide, hexylmethylphosphoric triamide, dimethylacetamide and N-methylcaprolactam or other N,N-disubstituted open-chain or cyclic carboxylic amides to be mentioned. Even a plurality of solvents can be used. Preference is given to N-methylpyrrolidone. The solvent or solvents are used in such an amount that the reaction mixture is easy to stir.

Suitable acids are virtually all inert inorganic acids. Preferably hydrochloric acid or diluted sulphuric acid are mentioned. In particular, hydrochloric acid is used to carry out the process according to the invention.

The process according to the invention is generally carried out at temperatures between 80° and 160° C. Preference is given to the temperature range between 90° and 140° C., in particular between 100 and 125. The reactions are usually carried out at atmospheric pressure.

To carry out the process according to the invention, 1 to 4 mol, preferably 2 to 3 mol, in particular 2 to 2.5 mol of sodium hydrogen sulphide or 1 to 4 mol, preferably 1 to 2 mol, in particular 1 to 1.5 mol sodium sulphide, respectively, are generally employed, per mol of ahlobenzene of the formula (II).

The process according to the invention is preferably carried out using sodium hydrogen sulphide. The reaction is carried in such a manner that the sodium hydrogen sulphide or sodium sulphide, respectively, is dissolved in the appropriate diluent and the water is removed at temperatures of about 160° C., for example by partial distillation with xylene or nitrogen. After cooling to the reaction temperature, the halobenzene of the formula (II) is added. The reaction is continued for a few hours (about 2 to 6 hours), and the solvent is subsequently distilled off. The residue is then taken up in water, and the filtrate is acidified with an acid and worked up in a conventional manner (cf. preparation examples). Novel thiophenols are those of the formula (Ia)

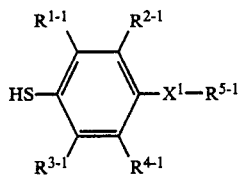

(Ia)

in which

R$^{1\text{-}1}$, R$^{2\text{-}1}$, R$^{3\text{-}1}$ and R$^{4\text{-}1}$ independently of each other each stand for hydrogen, halogen, nitro, alkyl, alkoxy, alkylthio, alkoxyalkyl, alkylthioalkyl, haloalkyl, haloalkoxy or alkylcarboxyl optionally substituted aryl or optionally substituted hetaryl, R$^{5\text{-}1}$ stands for alkyl, alkoxyalkyl, alkylthioalkyl haloalkyl, alkenyl, haloalkenyl, optionally substituted aryl or optionally substituted hetaryl and X$^1$ stands for carbonyl, sulpinyl or sulphonyl with the proviso that the compounds 4-acetylthiophenol bis-(4-thiophenyl)sulphone, 4-chloro-4'-thiobenzophenone and 4-chloro-4'-thiophenylphenylsulphone are excepted.

The compounds excepted in the formula (Ia) are known from DE-OS (German Published Specification) No. 2,156,345 and J. Org. Chem 28, 3077–3082 (1963).

Preference is given to thiophenols of the formula (Ia) in which

R$^{1\text{-}1}$, R$^{2\text{-}1}$, R$^{3\text{-}1}$ and R$^{4\text{-}1}$ independently of each other stand for hydrogen, fluorine, chlorine, bromine, iodine, nitro, $C_1$–$C_6$-alkyl, $C_1$–$C_6$-alkoxy, $C_1$–$C_6$-alkylthio, $C_1$–$C_4$-alkoxy-$C_1$–$C_6$-alkyl, $C_1$–$C_4$-alkylthio-$C_1$–$C_6$-alkyl, halo-$C_1$–$C_6$-alkyl halo-$C_1$–$C_6$-alkoxy or $C_1$–$C_6$-alkylcarboxyl, optionally substituted aryl having in each case 6 to 10 carbon atoms or optionally substituted hetaryl having 5 to 8 ring atoms, examples of aryl and hetaryl substitutents being halogen, nitro, $C_1$–$C_4$-alkyl, $C_1$–$C_4$-alkoxy, $C_1$–$C_4$-alkylthio and halo-$C_1$–$C_4$-alkyl, hetaryl having 1 or 2 identical or different heteroatoms such as nitrogen, sulphur or oxygen, and in particular standing for pyridyl or pyrimidyl substituted by the abovementioned substituents, and aryl in particular standing for phenyl or naphthyl substituted by the abovementioned substituents, R$^{5\text{-}1}$ stands for $C_1$–$C_{12}$-alkyl, $C_1$–$C_6$-alkoxy -$C_1$–$C_{12}$-alkyl, $C_1$–$C_6$-alkylthio-$C_1$–$C_{12}$-alkyl, halo-$C_1$–$C_{12}$-alkyl, $C_2$–$C_{10}$-alkenyl, halo-$C_2$–$C_{10}$-alkenyl, optionally substituted phenyl or naphthyl or optionally substituted hetaryl having 5 to 7 ring atoms, examples of phenyl, naphthyl and hetaryl substituents being $C_1$–$C_4$-alkyl, $C_1$–$C_4$-alkoxy, $C_1$–$C_4$-alkylthio and halo-$C_1$–$C_4$-alkyl, hetaryl having 1 or 2 identical or different heteroatoms such as nitrogen, sulphur or oxygen, hetaryl in particular standing for pyridyl or pyrimidyl substituted by the abovementioned substituents and X stands for carbonyl, sulphinyl or sulphonyl, with the proviso that the compounds 4-acetylthiophenol, bis-(4-thiophenyl) sulphone, 4-chloro-4'-thiobenzophenone and 4-chloro-4'-thiophenyl phenyl sulphone are excepted.

Particular preference is given to those compounds of the formula (Ia) in which

R$^{1\text{-}1}$, R$^{2\text{-}1}$, R$^{3\text{-}1}$ and R$^{4\text{-}1}$ independently of each other each stand for hydrogen, fluorine, chlorine, nitro, methyl, ethyl, n- or isopropyl, methoxy, ethoxy, methylthio, ethylthio, methoxymethyl, methoxyethyl, ethoxymethyl, ethoxyethyl, halo-$C_1$–$C_2$-alkyl, halo-$C_1$–$C_2$-alkoxy, methylcarboxyl, ethylcarboxyl, n-propylcarboxyl, iso-propylcarboxyl, and for, in each case, optionally substituted phenyl, pyridyl or pyrimidyl, examples of substituents being, in each case, fluorine, chlorine, nitro, methyl, ethyl, methoxy, methylthio and/or trifluoromethyl, R$^{5\text{-}1}$ stands for $C_1$–$C_{10}$-alkyl, $C_1$–$C_4$-alkoxy-$C_1$–$C_{10}$-alkyl, $C_1$–$C_4$-alkylthio-$C_1$–$C_{10}$-alkyl, halo-$C_1$–$C_{10}$-alkyl, $C_2$–$C_5$-alkenyl, halo-$C_2$–$C_5$-alkenyl, and for, in each case, optionally substituted phenyl, pyridyl or pyrimidyl, examples of substituents being fluorine, chlorine, nitro, methyl, ethyl, methoxy, methylthio and/or trifluoromethyl and X stands for carbonyl, sulphinyl or sulphonyl, with the proviso that the compounds 4-acetylthiophenol, bis-(4-thiophenyl)sulphone, 4-chloro-4'-thiobenzophenone and 4-chloro-4'-thiophenyl phenylsulphone are excepted.

Very particular preference is given to the compounds of the formula (Ia) in which R$^{1\text{-}1}$, R$^{2\text{-}1}$, R$^{3\text{-}1}$ and R$^{4\text{-}1}$ independently of each other each stand for hydrogen, fluorine, chlorine, methyl, methoxy, methylthio or trifluoromethyl, R$^{5\text{-}1}$ stands for methyl, ethyl, n- or isopropyl, n-, iso-, sec- or tert-butyl, n-pentyl, iso-pentyl, neopentyl, n-hexyl, iso-hexyl, neohexyl, n-heptyl, iso-heptyl, neo-heptyl, methylcarboxyl, ethylcarboxyl, allyl, methylvinyl, and for phenyl which is unsubstituted or monosubstituted to trisubstituted identically or differently by fluorine, chlorine, methyl, methoxy or trifluoromethyl, X$^1$ stands for carbonyl, sulphinyl, or sulphonyl, with the proviso that the compound 4-acetyl-thiophenol is excepted and that R$^{5\text{-}1}$ does not stand for 4-chlorophenyl.

Not only, the novel but also the known thiophenols of the formula (I) are valuable intermediates and are suitable for example for the synthesis of aryloxy(or thio) aminopyrimidines which are effective as herbicides and have been described in parallel patent applications.

Thus, to obtain novel aryloxy(or thio)aminopyrimidines of the formula (IV)

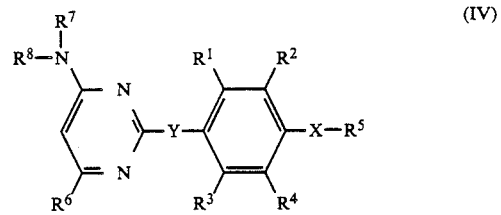

(IV)

in which

R$^1$, R$^2$, R$^3$, R$^4$, R$^5$ and X have the abovementioned meaning,

R$^6$ stands for hydrogen or alkyl optionally substituted by halogen, alkoxy and/or alkylthio, R$^7$ stands for hydrogen, alkyl, alkoxyalkyl, cycloalkyl or alkenyl, R$^8$ stands for hydrogen or alkyl or R$^7$ and R$^8$ together with a nitrogen atom to which they are attached can form a three- to six-membered ring with 1 or 2 further identical or different heteroatoms such as nitrogen, oxygen or sulphur, and Y stands for oxygen or sulphur, pyrimidine derivatives of the formula (V)

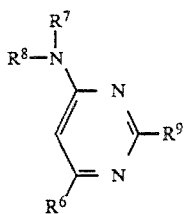

in which

R⁶, R⁷ and R⁸ have the abovementioned meaning and

R⁹ stands for halogen or alkylsulphonyl, in particular chlorine, methylsulphonyl or ethylsulphonyl, are reacted with thiophenols of the formula (I)

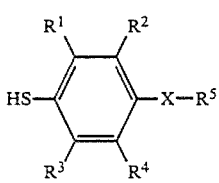

in which

R¹, R², R³, R⁴, R⁵ and X have the abovementioned meaning, or with thiophenols of the formula (VI)

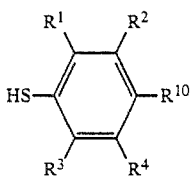

in which

R¹, R², R³ and R⁴ have the abovementioned meaning and

R¹⁰ stands for alkyl, alkoxyalkyl, alkylthioalkyl, haloalkyl, alkenyl or haloalkenyl, if desired, in the presence of a diluent such as, for example, N-methylpyrrolidone and, if desired, in the presence of an acid-binding agent such as, for example, sodium or potassium hydroxide at temperatures between 50° C. and 150° C.

This process is carried out by using, in general, approximately equimolar amounts of the reactants of the formula (V) or (VI) and (I). However, it is also possible to employ one or the other component in a large excess. The workup is carried out using conventional methods (cf. Preparation Examples).

The pyrimidine derivatives of the formula (V) are known or can be obtained by known methods of organic chemistry (cf. A. Weisberger: The Chemistry of Heterocyclic Compounds; The Pyrimidines, 1962 Interscience, New York).

The thiophenols of the formula (VI) are obtained by reacting the thiophenols according to the invention of the formula (Ib)

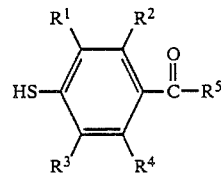

in which

R¹, R², R³, R⁴ and R⁵ have the abovementioned meaning, with reducing agents such as, for example, sodium borohydride in the presence of a diluent such as, for example, diethylene glycol dimethyl ether at temperatures between 20° C. and 140° C. (cf. Preparation Examples).

The thiophenols according to the invention of the formula (Ib) are covered by the formula (I) (X=carbonyl) and are described in that section.

PREPARATION EXAMPLES

Example I-1

2-chloro-4-acetylthiophenol

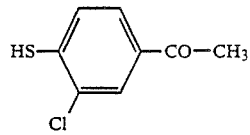

110 g (1.48 mol) of sodium hydrogen sulphide (NaSH·H₂O) are initially introduced together with 1 l of N-methylpyrrolidone and the water is removed at 160° C. with nitrogen. The mixture is cooled to 140° C. and 112 g (0.59 mol) of 3,4-dichloroacetophenone are added, and the mixture is reacted further at 160° C. for 3 hours, and N-methylpyrrolidone is distilled off. The residue is taken up in 1 l of water and filtered, and the filtrate is acidified at 0°–10° C. with half-concentrated hydrochloric acid. The precipitate is filtered off with suction, washed neutral and dried. Distillation under reduced pressure gives 99.8 g (90.7% of theory) of 2-chloro-4-acetylthiophenol of boiling point: 125°–130° C./0.1 mbar.

Example I-2

4-(neopentylcarbonyl)-thiophenol

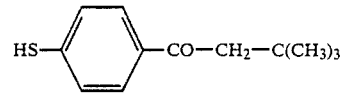

18.5 g (0.2 mol) of sodium hydrogen sulphide (NaSH·H₂O) in 100 ml of N-methylpyrrolidone are introduced and the water is removed by partial distillation with xylene. The mixture is cooled to 140° C., 21.05 g (0.1 mol) of 4-(neopentylcarbonyl)-chlorobenzene are added, and the mixture is further reacted at 160° C. for 3 hours and worked up as described in Example I-1 to give 14 g (70% of theory) of the desired product of boiling point: 110°–115° C./0.1 mbar.

Example I-3

4-(neopentylsulphonyl)-thiophenol

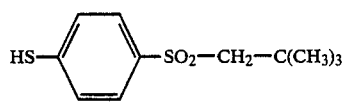

14.4 g (0.194 mol) of sodium hydrogen sulphite (NaSH·H₂O) in 120 ml of N-methylpyrrolidone are introduced and the water is removed at 160° C. with nitrogen. The mixture is cooled to 100° C., 20 g (0.081 mol) of 4-(neopentylsul-phonyl)-chlorobenzene are added, and the mixture is further reacted at 125° C. for 5 hours and the solvent is distilled off under reduced pressure. The residue is dissolved in 150 ml of water and acidified at 10°-20° C. with half-concentrated hydrochloric acid. The mixture is extracted with 100 ml of methylene chloride, the organic phase is washed neutral with water, dried with magnesium sulphate, concentrated and, after addition of 50 ml of toluene, distilled at 0.1 mbar up to an inside temperature of 130° C. to give 19 g of 4-(neopentylsulphonyl)-thiophenol of boiling point: 130° C./0.1 mbar; purity by gas chromatography: 98.6%=95% of theory.

In analogy to Examples I-1 to I-3 and using the general preparative details the following thiophenols of the formula (I) are obtained:

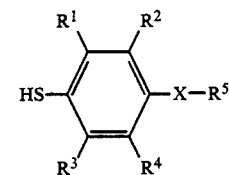

TABLE 1

| Example No. | $R^1$ | $R^2$ | $R^3$ | $R^4$ | $R^5$ | X | Boiling point (°C./mbar) Melting point °C. |
|---|---|---|---|---|---|---|---|
| 4 | H | H | H | H | —CH₃ | —CO— | 80–82/0.1 |
| 5 | H | H | H | H | —CH₂CH₂CH₃ | —CO— | 104–106/0.2 |
| 6 | H | H | H | H | —CH₂CH(CH₃)₂ | —CO— | 93–95/0.1 |
| 7 | H | H | H | H | —CH(CH₃)₂ | —CO— | 74–75 |
| 8 | Cl | H | H | H | —CH₂CH₂COOH | —CO— | 129–130 |
| 9 | Cl | H | H | CH₃ | —CH₃ | —CO— | 88–90 |
| 10 | H | H | H | H | –C₆H₅ | —CO— | 70–71 |
| 11 | Cl | H | H | H | –C₆H₅ | —CO— | 71–72 |
| 12 | H | H | H | H | –C₆H₄Cl | —CO— | 107–108 |
| 13 | H | H | H | H | —C(CH₃)=CH₂ | —CO— | 85–87/0.1 |
| 14 | H | H | H | H | —CH₂C(CH₃)₃ | —SO— | 112–116 |
| 15 | H | H | H | H | —CH₂CH₂C(CH₃)₃ | —CO— | |

Preparation example for compounds which are effective as herbicides:

Example IV-1

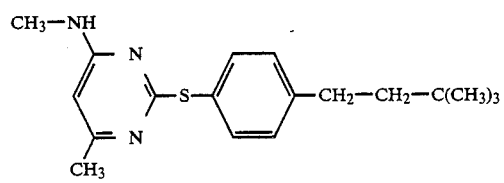

3.7 g (17 mmol) of 4-neohexyl-thiophenol in 20 ml of N-methylpyrrolidone are added in a nitrogen atmosphere to 1.18 g (21 mmol) of powdered potassium hydroxide and stirred for 15 minutes. After adding 3.42 g (17 mmol) of 4-methylamino-6-methyl-2-methylsulphonylpyrimidine, the mixture is heated at 120° C. for 90 minutes. The reaction mixture is poured into 150 ml of 1N sodium hydroxide solution and extracted with toluene, and the organic phase is dried and concentrated in vacuo. The residue is chromatographed with 3:1 cyclohexane/ethyl acetate to give, after crystallization from ether/n-hexane, 3.23 g (60.3% of theory) of the desired product of melting point 105° C.

Example IV-2

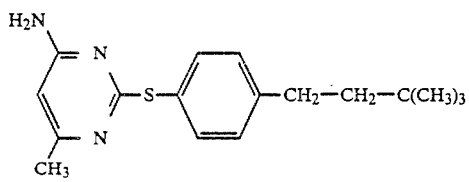

In a similar manner, as described under Example IV-1, the product IV-2 is obtained in a yield of 2.7 g (44.9% of theory) of melting point 111° C.

Example VI-1

4-(neohexyl)-thiophenol

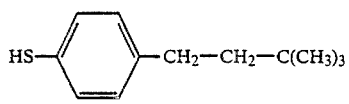

7.5 g (0.2 mol) of sodium borohydride in 140 ml of diethylene glycol dimethyl ether are initially introduced, and a solution of 41.6 g (0.2 mol) of 4-(neopentylcarbonyl)-thiophenol in 60 ml of diethylene glycol dimethyl ether are added at 30°-40° C. The mixture is further reacted at 120° C. for 2 hours, 100 ml of water are added with ice-cooling, the mixture is acidified with 20% strength sulphuric acid, and another 200 ml of water are added. The reaction mixture is now extracted with 250 ml of methylenechloride, the organic phase is extracted with 250 ml of water, dried over magnesium sulphate and distilled through a split ring column to give 23 g (60% of theory) of 4-(neohexyl)-thiophenol of boiling point 98° C./0.4 mbar.

Use example

In the use example which follows, the compound shown below was used as a comparative substance:

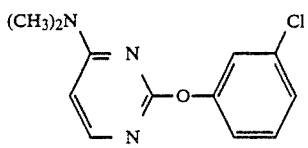

2-(3-chlorophenoxy)-4-dimethylaminopyrimidine (known from EP-A-1,187/Example 28)

Example A

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, the compounds according to the preparation Examples IV-1 and IV-2, for example, show a significantly better herbicidal activity than the comparison substance (A).

TABLE A

| | | Post-emergence test/Greenhouse | | | | | |
|---|---|---|---|---|---|---|---|
| Active ingredient | Amount of active ingredient used g/ha | Wheat | Amaranthus | Chenopodium | Galinsoga | Sinapis | Setaria |
| A (known from EP-A-1,187) | 250 | 0 | 0 | 0 | 0 | 0 | 0 |
| IV-1 | 125 | 10 | 100 | 90 | 100 | 100 | 90 |

TABLE A-continued

| | | Post-emergence test/Greenhouse | | | | | |
|---|---|---|---|---|---|---|---|
| Active ingredient | Amount of active ingredient used g/ha | Wheat | Amaranthus | Chenopodium | Galinsoga | Sinapis | Setaria |
| IV-2 | 125 | 10 | 100 | 100 | 100 | 100 | 100 |

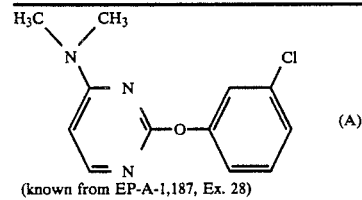

(A)

(known from EP-A-1,187, Ex. 28)

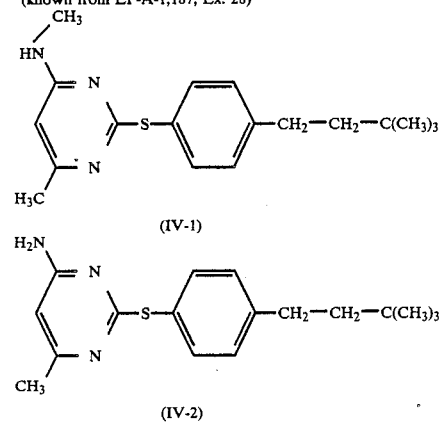

What is claimed is:

1. Process for preparing a thiophenol of the formula

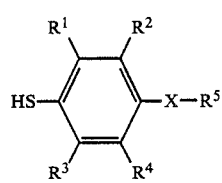

in which

R$^1$, R$^2$, R$^3$ and R$^4$ each independently represent hydrogen, halogen, nitro, alkyl, alkoxy, alkylthio, alkoxyalkyl, alkylthioalkyl, haloalkyl or haloalkoxy, optionally substituted carbocyclic aryl or optionally substituted hetaryl said optional substituents being halogen, nitro, C$_1$-C$_4$-alkyl, C$_1$-C$_4$-alkoxy, C$_1$-C$_4$-alkylthio and halo C$_1$-C$_4$-alkyl and said hetaryl having 5 or 6 ring members and 1 or 2 identical or different nitrogen, oxygen or sulfur atoms, R$^5$ stands for alkyl, alkoxyalkyl, alkylthioalkyl, haloalkyl, alkenyl, haloalkenyl, optionally substituted carbocyclic aryl or optionally substituted hetaryl said optional substituents being halogen, nitro, C$_1$-C$_4$-alkyl, C$_1$-C$_4$-alkoxy, C$_1$-C$_4$-alkylthio and halo C$_1$-C$_4$-alkyl and said hetaryl having 5 or 6 ring members and 1 or 2 identical or different nitrogen, oxygen or sulfur atoms, and X stands for carbonyl, sulphinyl or sulphonyl wherein a halobenzene of the formula

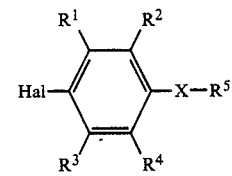

in which

Hal represents halogen, is reacted with a reactant consisting essentially of sodium hydrogen sulphide or sodium sulphide at a temperature between 80° and 160° C. in the presence of a diluent to form a compound of the formula

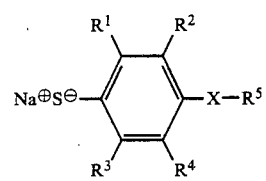

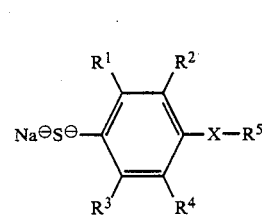

followed by the addition of an acid to form the thiophenol.

2. The process according to claim 1, wherein the acid is hydrochloric acid or diluted sulphuric acid.

3. The process according to claim 1, wherein 1 to 4 mol of sodium hydrogen sulphide are used per mole of halobenzene.

4. The process according to claim 1, wherein 1 to 4 mol of sodium sulphide are used per mole of halobenzene.

* * * * *

UNITED STATES PATENT AND TRADEMARK OFFICE
CERTIFICATE OF CORRECTION

PATENT NO. : 4,980,510
DATED : December 25 1990
INVENTOR(S) : Hagemann et al.

It is certified that error appears in the above-identified patent and that said Letters Patent is hereby corrected as shown below:

Title Page        ABSTRACT: Line 1 delete " t,10 " and substitute

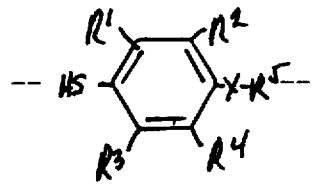

Col. 14, line 55     Delete 2nd formula " 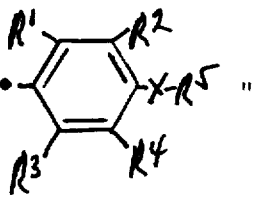 "

Signed and Sealed this

Twenty-ninth Day of September, 1992

Attest:

DOUGLAS B. COMER

Attesting Officer      Acting Commissioner of Patents and Trademarks